US00PP28443P3

(12) United States Plant Patent
Byrne et al.

(10) Patent No.: US PP28,443 P3
(45) Date of Patent: Sep. 26, 2017

(54) NECTARINE TREE NAMED 'SMOOTH DELIGHT TWO'

(50) Latin Name: *Prunus persica*
Varietal Denomination: Smooth Delight Two

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 43 days.

(21) Appl. No.: 14/544,522

(22) Filed: Jan. 13, 2015

(65) Prior Publication Data

US 2016/0205830 P1 Jul. 14, 2016

(51) Int. Cl.
*A01H 5/08* (2006.01)

(52) U.S. Cl.
USPC ..... Plt./190

(58) Field of Classification Search
USPC ..... Plt./190
See application file for complete search history.

(56) References Cited

U.S. PATENT DOCUMENTS

PP9,332 P 10/1995 Zaiger et al.
PP9,871 P 4/1997 Sherman

OTHER PUBLICATIONS

Philips. AgriLife Today. Dec. 30, 2013.*
The Brooks and Olmo Register of Fruit and Nut Varieties, 3rd Ed., American Society of Horticultural Science Press, Alexandria, VA, 1997.
Andrews et al.; 'FlordaKing' peach; HortScience; 1979; pp. 81-82; vol. 14.
Byrne et al.; 'TexKing', an Early Ripening, Medium-chill Peach; HortScience; Apr. 2004; pp. 442-443; vol. 39.

* cited by examiner

*Primary Examiner* — Keith Robinson
(74) *Attorney, Agent, or Firm* — Ramey & Schwaller, LLP

(57) ABSTRACT

Disclosed is a new variety of *Prunus persica* named 'Smooth Delight Two'. This new variety, which requires 350-400 chilling units of dormancy, is a nectarine tree of early season maturity, which ripens in early to mid-May in the medium chill zone of Texas and produces yellow fleshed sub acid fruit that are firm, attractively colored, and suitable for both local and regional fresh fruit markets.

5 Drawing Sheets

BACKGROUND OF THE INVENTION

Field of the Invention

This invention relates to nectarine trees and, more specifically, to nectarine trees referred to as a variety of *Prunus persica* named 'Smooth Delight Two', which requires 350 to 400 chilling units of dormancy, produces an high quality, firm clingstone sub-acid yellow fleshed nectarine that matures early in the season.

SUMMARY OF THE INVENTION

The 'Smooth Delight Two' (TX2B233LN) nectarine is characterized as to novelty and is otherwise noteworthy by producing a yellow nectarine that ripens in the early season; is considered good to high quality; and which is firm and has an attractive coloration. In this regard, the present variety of nectarine tree bears fruit that are ripe for commercial harvesting the second week of May when grow in south central Texas. 'Smooth Delight Two' ripens 5-7 days after 'Flordaking' (not patented, Andrews et al., 1979) and about a week before 'TexKing' (U.S. Plant Pat. No. 14,627; Byrne and Bacon, 2004).

ORIGIN OF THE VARIETY

The present nectarine tree was the result of an ongoing Stone Fruit Breeding Program of Texas A & M University, College Station, Brazos County, Tex. To this end, controlled crosses are made each year in order to produce seedling populations from which improved progenies are evaluated and selected.

The seedling 'TX2B233LN' was identified at the Texas A & M University Horticultural Farm in College Station, Tex. and was chosen from a population of seedlings that resulted from seed from a cross between the female parent 'Sunmist' (U.S. Plant Pat. No. 9,871, Apr. 29, 1997) and the male parent 'Arctic Star' (U.S. Plant Pat. No. 9,332, Oct. 17, 1995). Resulting seed from this cross were planted at the Texas A & M University Horticultural Farm in College Station, Tex. 'TX2B233LN' was marked for subsequent observation and noted as having exceptional characteristics. Two-year and older trees of the variety were subsequently evaluated during the 2005 through 2010 fruit growing seasons in both California (Clovis) and Texas (Floresville and College Station).

ASEXUAL REPRODUCTION OF THE VARIETY

'TX2B233LN' was bud grafted onto virus-tested Nemaguard (not patented, Brooks and Olmo 1997) peach rootstock in June 2003 at the nursery site in Oakdale, Calif. The variety was subsequently planted at the experimental orchard in the central portion of the San Joaquin Valley, near Fowler, Fresno County, Calif. and in two sites in Texas (College Station and Floresville). Fruit from the resulting propagation has been evaluated during the period from 2005 to 2010 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographic drawings and depicts the plant in its fifth growing season by the best possible color representation using color photography, wherein.

BOTANICAL DESCRIPTION OF THE VARIETY

Figure 1:
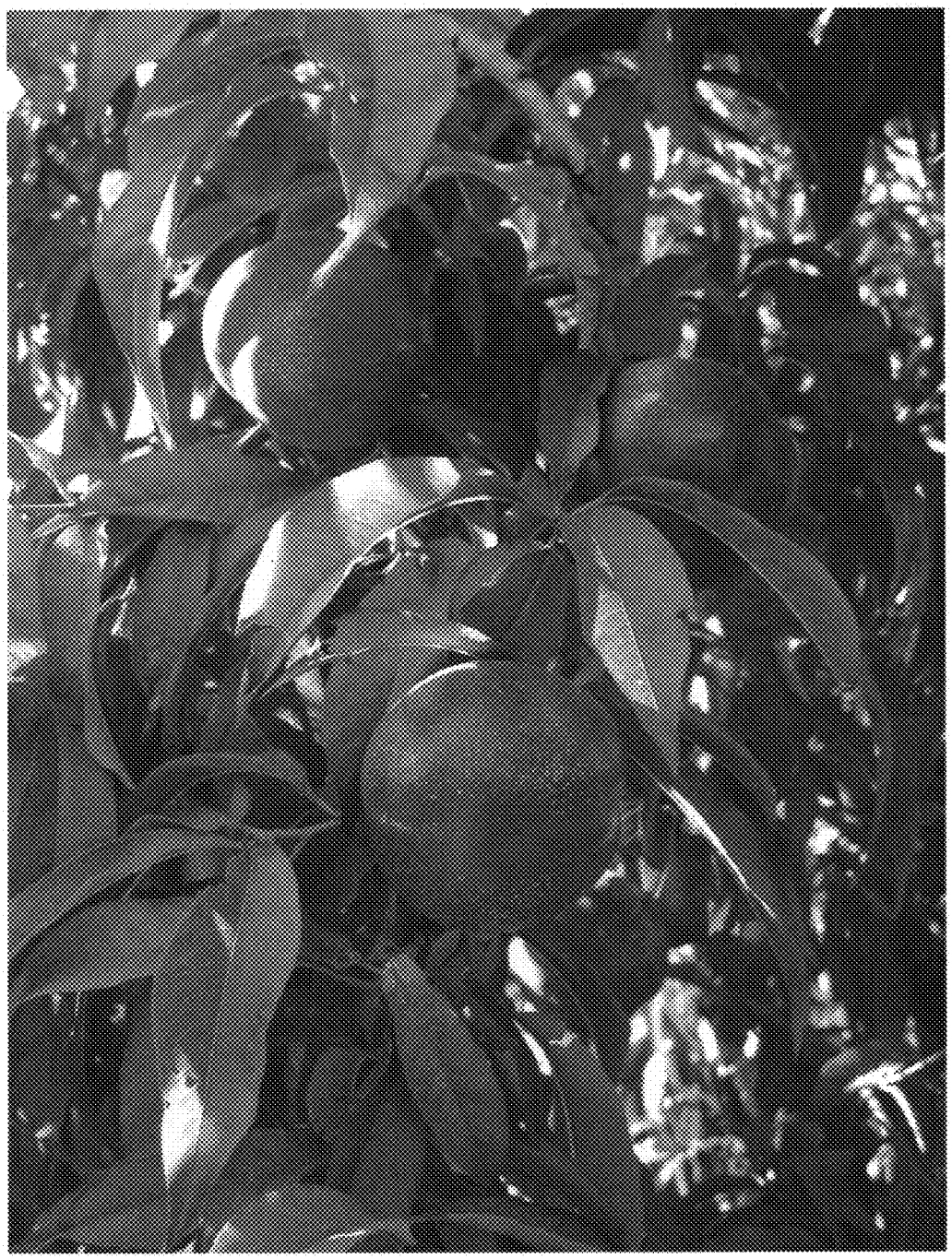
FIG. 1. A color photograph of a characteristic twig bearing typical leaves and several mature fruit showing their external coloration sufficiently matured for harvesting and shipment of 'Smooth Delight Two'.
Figure 2:
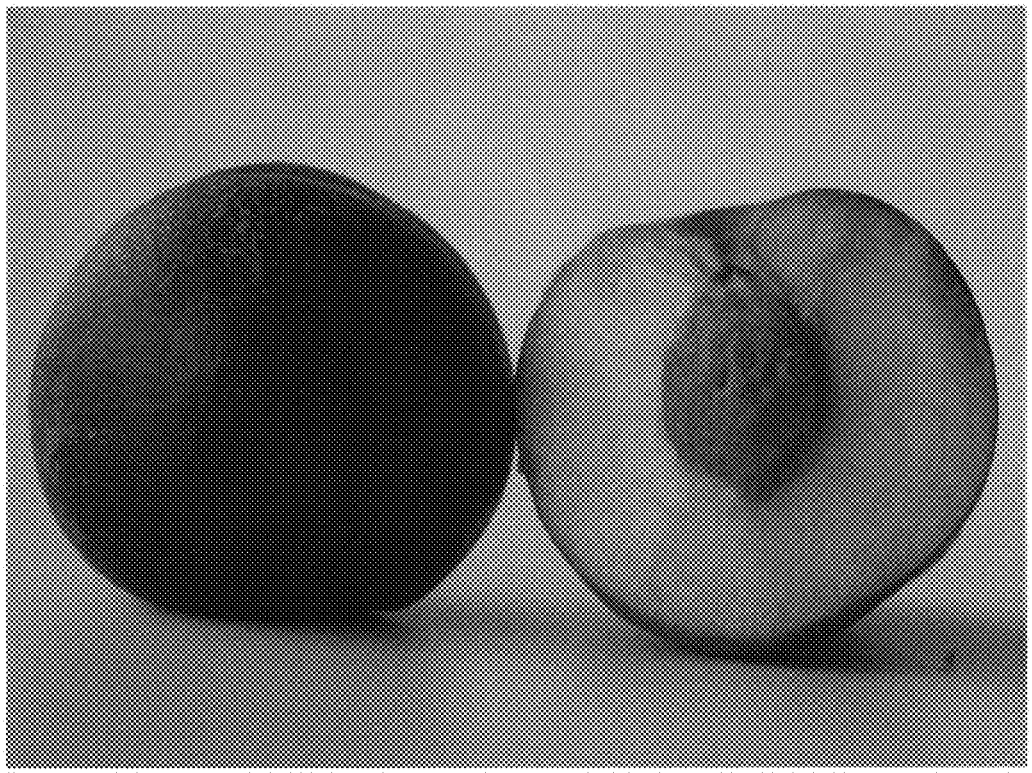
FIG. 2. 'Smooth Delight Two' grown in Floresville, Tex. showing external and internal color.
Figure 3:
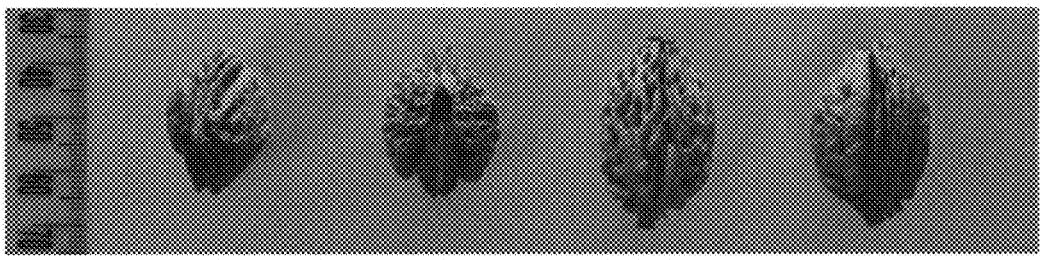
FIG. 3. Color photographs of the endocarps of 'Smooth Delight Two' nectarine. The ruler is demarcated in millimeters.
Figure 4:
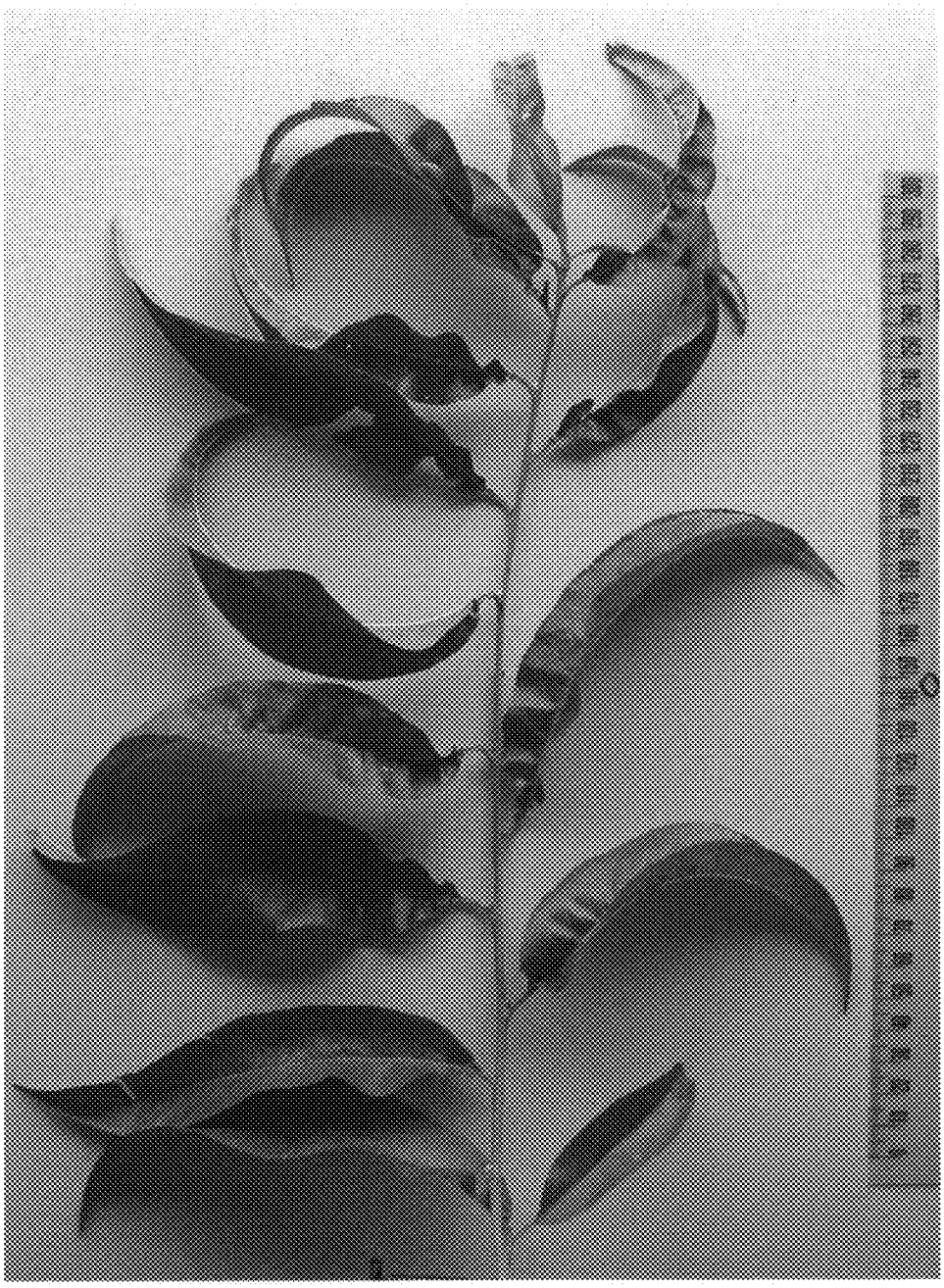
FIG. 4. A shoot showing the leaves of the 'Smooth Delight Two' nectarine. The ruler is demarcated in millimeters.
Figure 5:
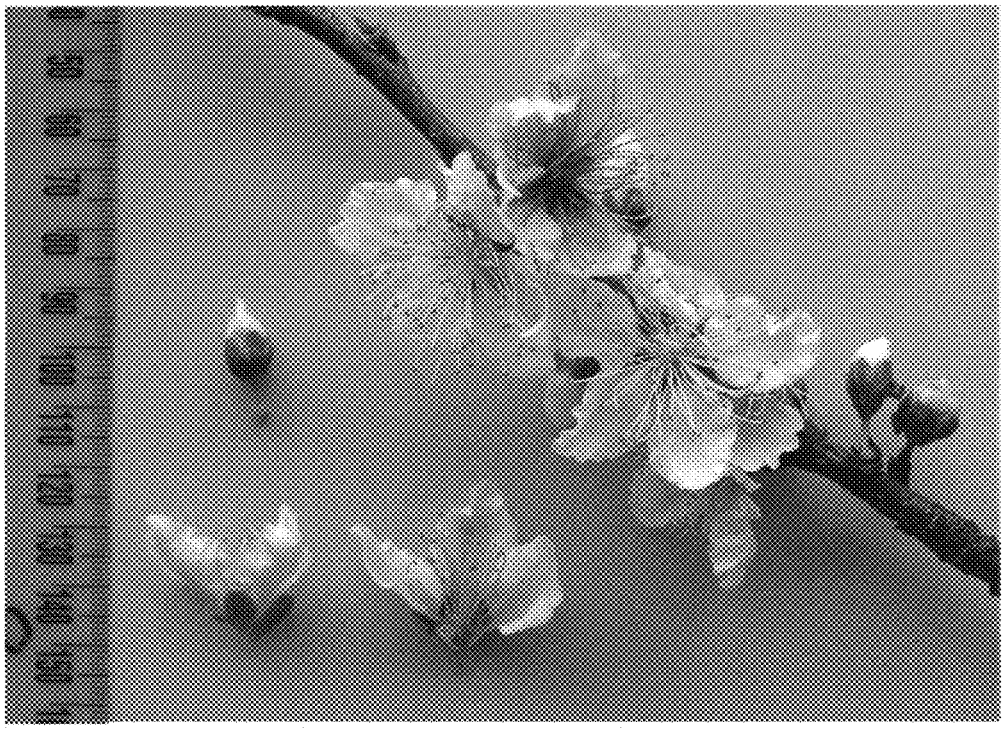
FIG. 5. The showy flowers of 'Smooth Delight Two'. The ruler is demarcated in millimeters.

Referring more specifically to the pomological details of this new and distinct variety of nectarine tree, the following has been observed under the ecological conditions prevailing at the experimental orchards in College Station, Tex., Floresville, Tex. and Fowler, Calif. All major color code designations are by reference to The R.H.S. Colour Chart (2001) provided by The Royal Horticultural Society of Great Britain. Colors are approximate as color depends on horticultural practices such as light level and fertilization rate, among others.

Tree:

*Size*.—Generally average to above average as compared to other common peach and nectarine cultivars ripening in the early season of maturity.

*Height*.—10 feet (3.05 m) at the end of the 2012, their fifth growing season.

*Width*.—6 feet (1.83 m) at the end of the 2012, their fifth growing season.

*Vigor*.—High.

*Density*.—Medium to high.

*Productivity*.—Productive.

*Shape*.—The 'Smooth Delight Two' exhibits a generally spreading growth habit typical of commercial varieties of nectarine such as 'TexKing' (U.S. Plant Pat. No. 14,627 and 'TexRoyal' (not patented, Byrne and Bacon, 1991).

*Current season growth*.—The current season growth for the new variety was approximately 3.8 feet (1.2 m).

*Regularity of bearing*.—Regular, and considered hardy under typical climatic conditions in the low and medium chill zones of Texas and in the central San Joaquin Valley, Calif. conditions.

Trunk:

*Size*.—Approximately 3.8 inches (9.53 cm) in diameter and 13.0 inches (33.02 cm) in circumference when measured at a distance of approximately 12 inches (30.5 cm) above the soil level, at the end of the 2012 growing season on a five-year old tree.

*Bark texture*.—Considered moderately rough with numerous folds of papery scarf-like skin being present.

*Bark coloration*.—Variable, colors present are 200D and N200C-D of the Brown Group and 201C-D of the Grey Group.

Branches:

*Size*.—Considered medium for the variety.

*Thickness and length*.—Average (about 6.2 cm in diameter as measured 10 cm from the trunk on a five-year old tree) as compared to other varieties. The length of the branches are limited by pruning to a 3 to 5 foot (approximately 0.9 to 1.5 m) depending on its position in the tree.

*Surface texture*.—Average and appearing furrowed on wood that is several years old.

*Lenticels*.—Numerous flat, oval lenticels present. The lenticels range in size from approximately 4 to 6 mm in width and were approximately 1-2 mm in height.

*Current season shoots*.—Surface texture — Substantially glabrous.

*Internode length*.—Approximately 2.1 cm as measured in the middle of a current season stem.

*Color of mature branches*.—The predominant RHS colors are 200D and N200C-D of the Brown Group.

*Current season shoots*.—Color (RHS colors) — Light green (137B-D, 138A-B, 141C of Green group and 144A-C, 146B-C, 147B-C, 148A-B and 152A of the Yellow Green Group) with some reddish-brown coloration appearing on exposed surface of the shoots (165A-B, 166A-B, 174A, and 175A-C of the Grey Orange group). The upper exposed surface of the current season growth exhibit medium intensity of anthyocyanins.

Leaves:

*Size*.—Considered average for the species. Leaf measurements have been taken from vigorous upright current season growth approximately at mid-shoot.

*Leaf length*.—Approximately 153 to 170 mm.

*Leaf width*.—Approximately 35 to 41 mm.

*Leaf thickness*.—Approximately less than 1 mm.

*Leaf form*.—Lanceolate.

*Leaf tip form*.—Acuminate.

*Leaf upper surface color*.—Green, approximately 137A of the Green Group.

*Leaf lower surface color*.—Green, approximately 137C-D of the Green Group.

*Leaf mid-vein color*.—Yellow-green, approximately 145C-D of the Yellow-Green Group

*Leaf margins*.—

*Form*.—Considered crenate/crenulate.

*Uniformity*.—Considered generally uniform.

*Leaf petioles*.—

*Size*.—Considered medium long.

*Length*.—Approximately 12 to 13 mm.

*Thickness*.—Approximately 1 to 2 mm.

*Color*.—Pale green (Yellow-Green Group N144C).

*Leaf glands*.—

*Size*.—Approximately 1 mm in height and 1 to 1.5 mm in width.

*Number*.—Generally 0-2 per leaf.

*Type*.—Reniform.

*Color*.—Medium brown (N199D of the Grey-Brown Group).

*Leaf stipules*.—Early deciduous.

*Length*.—Approximately 10-16 mm.

*Width*.—Light to medium green (Yellow-Green Group 144C-D and N144C-D), developing a red color upon maturity (Greyed-Red Groups 179A, 180A-B, and 181A).

*Ratio of wood (leaf) buds to flowering buds*.—1 to 2 flower buds per vegetative bud.

Flowers:

*Floral buds*.—

*General*.—The floral buds are considered to be medium large in size, conic in form, and slightly appressed relative to the bearing shoot.

*Color*.—The bud scales are dark brown in color with green and red coloration, (approximately Greyed-Purple Group 183C-D, Greyed-Green Group 194 B-C and the Brown Group 200A-D). The buds are considered hardy under typical climatic conditions in the low and medium chill zones of Texas and in the central San Joaquin Valley, Calif.

*Length*.—Approximately 6 to 7 mm.

*Width*.—Approximately 3 to 4 mm.

*Blooming type*.—It bloomed in mid February in Floresville, Tex., 4-6 days 'Flordaking' (not patented), 'TexKing' (U.S. Plant Pat. No. 14,627) and with or 1-2 days after 'Sunraycer' (not patented, Sherman et al., 1995). It is estimated to require between 350 and 400 chilling units to break winter dormancy.

*Flower type*.—Showy.

*Flower size*.—Flower diameter at full bloom is approximately 45 to 50 mm. The length of the flower at the pink bud stage before opening ranges from 15 to 18 mm.

*Bloom quantity*.—Considered abundant.

*Flower bud frequency*.—Normally 1 to 2 per node.

*Petal size*.—

*General*.—Considered medium large for the species.

*Width*.—Approximately 14 to 17 mm.

*Length*.—Approximately 19 to 22 mm.

*Petal form*.—Broadly ovate.

*Petal count*.—Nearly always 5.

*Petal color*.—Light pink when young (RHS White Group N155B-C), becoming darker near the petal claw (RHS Red-Purple Group 64D).

*Petal claw*.—

*Form*.—The claw is considered truncate in shape and has a medium large size when compared to other varieties.

*Length*.—Approximately 1.5 to 2 mm.

*Width*.—Approximately 1 to 1.5 mm.

*Petal margins*.—Generally considered variable, from nearly smooth to slightly undulate.

*Petal apex*.—Generally — The petal apices appear slightly domed.

*Flower pedicel*.—

*Length*.—Considered present, and having an average length of approximately 4.5 to 6 mm.

*Thickness*.—Considered average, approximately 0.5 to 1 mm.

*Color*.—A light green (RHS Yellow-Green Group N144A-D).

*Floral nectaries*.—

*Color*.—Dull orange (RHS Greyed-Orange Group 170B-C).

*Calyx*.—

*Surface texture*.—Generally glabrous.

*Color*.—A brownish red (approximately RHS Greyed-Red Group 178A-B).

*Sepals*.—

*Surface texture*.—The surface has a short, fine, and wooly texture.

*Size*.—Slightly larger than average and ovate in form. Approximately 6.5-7.0 mm in length and 6.1-7.00 mm in width at the pink bud stage of flower development.

*Color*.—A dull orange-red (approximately RHS Greyed-Orange Group 176A-B and 177A).

*Anthers*.—

*General*.—Average in size for the species. Approximately 1 mm in length and 0.4-0.5 mm in width.

*Color*.—Golden yellow with orange (approximately RHS Yellow-Orange Group 17A-B and Orange-Red Group 30A-C).

*Pollen production*.—Pollen is abundant, and is a yellow color approximately RHS Yellow-Orange Group 21B.

*Filaments*.—Size — Variable in length, approximately 14 to 17 mm, with the filaments slightly shorter than the pistil. The stamens are generally below the pistil and do not protrude when the flowers are at the pink bud stage of development.

*Color*.—White with a very light pink (approximately RHS White Group N155B-D) and darkening with advanced maturity.

*Pistil*.—

*General*.—Average in size, but slightly longer, relative to the general anther height, overall.

*Length*.—Approximately 19 to 22 mm, including the ovary.

*Color*.—Considered a very light yellow with green when young (approximately RHS Green-Yellow Group 1B and Yellow Group 4B-C), and becoming slightly darker with advancing senescence (approximately Red-Purple Group 64A-B).

*Pubescence*.—Absent, the pistil including the ovary is not pubescent.

Fruit:

*Maturity when described*.—The present variety of fruit is described, as it would be found in its firm ripe condition at full commercial maturity. Under the ecological conditions prevailing in the medium chill zone of Texas 'Smooth Delight Two' ripens in early to mid-May, 4-5 days after 'Flordaking' (not patented) and about a week before 'TexKing' (U.S. Plant Pat. No. 14,627).

*Size*.—General — Medium to medium large for the season and considered uniform.

*Average cheek diameter*.—Approximately 60 to 63 mm.

*Average suture diameter*.—Approximately 58 to 61 mm.

*Average axial diameter*.—Approximately 59 to 64 mm.

*Fruit form*.—Generally quite ovate in its lateral aspect.

*Fruit suture*.—Generally, the suture appears as a thin line and/or indentation that extends from the base to the apex, and appears deeper at the apex, forming a shallow basin at the apical point. No apparent callusing or stitching exists along the suture line.

*Color*.—Medium to dark red (Red Group 46A-B).

*Ventral surface*.—Form — Considered uniform.

*Stem cavity*.—Size — Considered average for the species.

*Length*.—Approximately 14 to 19 mm.

*Width*.—Approximately 19 to 22 mm.

*Depth*.—Approximately 9 to 14 mm.

*Fruit base*.—Flat.

*Fruit apex*.—Flat.

*Fruit stem*.—Length — 10 to 14 mm. Thickness — 2 to 4 mm. Color — Medium to light green (Yellow-Green Group 144A-C).

*Fruit skin*.—Generally considered medium or average in thickness. Surface Texture — Smooth. Skin Acidity — Considered neutral. Tenacious to Flesh — Yes at commercial maturity. Tendency to Crack — Generally resistant to cracking as compared to other varieties. Skin Color — Generally — Variable, with approximately (70%) to very high (90% ) percentage of the skin surface covered with blush as described under Blush Color below. Pubescence — The glabrous skin has a medium glossiness. Blush Color — This red blush (Red Group 46A) has many degrees of shading and blending. Skin Ground Color — Medium to light yellow (Yellow Group 2A-B).

*Flesh color*.—Medium to pale orange (Yellow-Orange Groups 20A and 21B).

*Stone cavity color*.—Pale orange (Yellow-Orange Group 20A).

*Flesh texture*.—Generally, the flesh is considered firm at commercial maturity.

*Ripening*.—Generally the fruit of the present variety ripens evenly.

*Flavor*.—Considered very sweet with sub acid flavor.

*Aroma*.—Pleasant and reasonably abundant.

*Eating*.—Generally considered very good to excellent, particularly for an early ripening variety.

Stone:

*Attachment*.—Clingstone (strongly adherent) at commercial maturity.

*Stone size*.—Generally considered medium to medium-large relative to the ratio of stone to fruit size.

*Length*.—Approximately 32 to 34 mm.

*Width*.—Approximately 25 to 27 mm.

*Thickness*.—Approximately 17 to 20 mm.

*Stone form*.—Round.

*Stone base angle*.—Medium to Wide.

*Apex shape*.—Wide.

*Stone shape*.—Varies from ovoid to elongated.

*Stone surface*.—

*Surface texture*.—Single pits and rosettes of pits.

*Ridges*.—A few fine ridges are present basally, and converge towards the base of the stone.

*Ventral edge*.—Medium.

*Dorsal edge*.—Shape — Grooved and having moderately rough edges.

*Stone color*.—The color of the dry stone is light brown (RHS 159A of the Orange-White Group and 164D, 165C-D, 166D and 167C-D of the Greyed-Orange Group). The color of the inside surface of the endocarp is primarily RHS 158A of the Yellow-White Group, 159A-B of the Orange-White Group and 164D and 165D of the Greyed-Orange Group.

*Tendency to split*.—Splitting is uncommon.

*Kernel*.—The kernel fills the endocarp at harvest and measures approximately 6-7 mm in thickness, 10-12 mm in width, and 17-19 mm in length. When dried the shriveled kernels measure approximately 2-4 mm in thickness, 9 mm in width, and 16-17 mm in length. The colors of the shriveled kernels are primarily Greyed-Orange Group 165B-C.

*Use*.—The subject variety, 'Smooth Delight Two', is considered to be a nectarine tree of early-season maturity, which produces fruit which are firm, attractively colored, yellow-fleshed, and sub acid flavor which are useful for both local and regional fresh fruit markets.

*Keeping quality*.—Good.

*Resistance to insects and disease*.—No particular susceptibilities or resistances were noted or claimed.

*Shipping quality*.—Average. Although the new variety of peach tree possesses the described characteristics when grown under the ecological conditions prevailing in the low and medium chill zones of Texas and in Fowler, Fresno County, Calif., it will be understood that variations of the usual magnitude and characteristics incident to the changes in growing conditions, fertilization, pruning, and pest control are to be expected.

REFERENCES

Andrews, C. P., W. B. Sherman, and P. M. Lyrene. 1979. 'Flordaking' peach. HortSciencе 14:81-82.

Anon. 2001. RHS Colour Chart. The Royal Hort. Soc., London.

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortSciencе 26(10): 1338-1340.

Byrne, D. H. and T. A. Bacon. 2004. 'TexKing', an early ripening medium chill peach. HortSciencе 39: 442-443. U.S. Plant Pat. No. 14,627. Mar. 23, 2004.

Sherman. W. B. 1997. Nectarine tree called 'Sunmist'. U.S. Plant Pat. No 9,871. Apr. 29, 1997.

Sherman, W. B., P. C. Andersen, and P. M. Lyrene. 1995. 'Sunmist' nectarine. HortSciencе 30(1): 155.

Sherman, W. B., P. C. Andersen, and P. M. Lyrene. 1995. 'Sunraycer' nectarine. HortSciencе 30(1): 154.

Zaiger, C., G. Zaiger, L. M. Gardner, and G. Zaiger. 1994. Nectarine tree 'Arctic Star'. U.S. Plant Pat. No. 9,332, Oct. 17, 1995.

We claim:

1. A new and distinct *Prunus persica* tree, substantially as illustrated and described herein.

* * * * *